(12) United States Patent
Goumont et al.

(10) Patent No.: US 6,242,143 B1
(45) Date of Patent: Jun. 5, 2001

(54) METHOD AND DEVICE FOR THE PROCESSING OF SILVER HALIDE PHOTOGRAPHIC MATERIALS

(75) Inventors: Claude G. Goumont, Mellecey Germolles; Jacques Roussilhe, Virey le Grand, both of (FR)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/495,574

(22) Filed: Feb. 1, 2000

Related U.S. Application Data

(63) Continuation-in-part of application No. 09/273,034, filed on Mar. 19, 1999, now abandoned.

(30) Foreign Application Priority Data

Mar. 24, 1998 (FR) .................................................. 9803864

(51) Int. Cl.⁷ ....................................................... G03C 5/31
(52) U.S. Cl. .............................................. 430/30; 430/399
(58) Field of Search ....................................... 430/30, 399

(56) References Cited

U.S. PATENT DOCUMENTS

| | | | |
|---|---|---|---|
| 4,857,750 | 8/1989 | Millis et al. | 250/573 |
| 5,489,961 | 2/1996 | Burbury et al. | 354/298 |

FOREIGN PATENT DOCUMENTS 0 585 792 A2   3/1994   (EP) .

*Primary Examiner*—Hoa Van Le

(57) ABSTRACT

This invention relates to a method and a device for the processing of silver halide photographic materials. The method of the invention includes accurately measuring the concentration of a developing agent in a photographic developing solution to monitor the activity of the bath and/or the need to replenish it. This measurement is carried out using spectrophotometric means.

3 Claims, 3 Drawing Sheets

METHOD AND DEVICE FOR THE PROCESSING OF SILVER HALIDE PHOTOGRAPHIC MATERIALS

CROSS-REFERENCE TO RELATED APPLICATIONS

This is a continuation-in-part of application Ser. No. 09/273,034, filed Mar. 19,1999 now abandoned, titled "METHOD AND DEVICE FOR THE PROCESSING OF SILVER HALIDE PHOTOGRAPHIC MATERIALS" by Goumont et al.

FIELD OF THE INVENTION

This invention relates to the treatment of silver halide photographic materials for the purpose of converting the latent images obtained by light exposure into developed, fixed and stabilized visible images.

PRIOR ART

The processing of photographic materials comprises a development step followed by a fixing step in the case of black-and-white development. The development step is carried out by immersion of the exposed photographic material in a developing bath containing a silver halide developing agent, the function of which is to reduce the exposed silver halides to metallic silver. After fixing, the photographic material is washed and dried.

During use the developing bath becomes gradually depleted in developing agent through the silver halide development reaction, and also by additional oxidation of the developing agent. This consumption of the developing agent, and the ensuing decrease in the concentration of the developing agent, causes the activity of the developing bath to decrease, thereby adversely affecting the sensitometric characteristics of the processed photographic materials. A way to make up for this loss of activity is to add to the 'seasoned' developing bath a certain amount of new developing solution, known as replenishing solution. However, the optimum timing of replenishment and the optimum quantities of replenishing solution to be added are difficult to determine. This is because a photofinishing laboratory treats a wide range of films and so the quantities of replenishing solution are in practice set at values that are significantly higher than is necessary. Clearly, it is desirable to add the minimum quantity of replenishing solution that is compatible with the maintenance of the specified sensitometric characteristics. Another positive outcome of minimizing replenishment is a reduction in the volume of effluent. The problem therefore is to be able to know when to replenish the developing solution, i.e., to determine when the activity of the developing bath is too low to ensure that the sensitometric characteristics will be maintained at the values that are specified for any particular photographic process. An essential parameter of the developing bath activity is the concentration of developing agent, which therefore has to be measured.

Various methods are known for measuring the concentration of developing agents. Many of these methods require prior extraction of the developing agent, and so are not suitable for preferably automated in-process monitoring of the concentration of a developing agent throughout the photographic processing. This extraction has been deemed necessary owing to the complex composition of the seasoned developing bath, and the presence in it of a large number of substances liable to react with analytical reagents or respond to analytical tools. The methods for determining the concentration of the developing agent are chemical, e.g., colorimetry, electrochemical, e.g., voltametry, or physical, e.g., chromatography. These methods are described in 'Chimie et Physique Photographiques' by P. Glafkidèds, 5th edition, pages 171–178 and 943–944. For on-line determinations, measuring the optical density of the developing bath has also been advocated. A new developing solution is limpid and pale yellow, whereas after a certain time in use it becomes turbid and dark in color. The increase in optical density can therefore be correlated with the seasoning of the developer, affording a way of determining when the developer has to be replenished. Such a method is described, for example, in U.S. Pat. No. 5,489,961. However, it is not a direct accurate measurement of the concentration of the developing agent, which is the main parameter that the activity of the developing bath depends on. Clearly then, the measurement of the concentration of the developing agent has to meet two conditions: the measurement must be accurate, and the measurement has to be performed on-line in a simple way, so that the result of this measurement can be exploited, especially to order replenishing of the developer if necessary.

The object of this invention is to provide a method that solves this problem.

SUMMARY OF THE INVENTION

There is provided a method comprising developing a previously exposed silver halide photographic material, using a developing solution containing a first silver halide developing agent, wherein the developing activity of which is monitored by measuring the concentration of said developing agent by ultraviolet spectrophotometry.

There is also provided a device for monitoring the developing activity of one or more photographic processing lines, said device comprising a system for measuring the concentration of a developing agent by spectrophotometry, and means to preselect the range of wavelength of the spectrophotometric measurement according to the developing agent the concentration of which is to be measured.

The method of the invention is based on the fact that certain constituents of the developing baths, especially the developing agents, absorb electromagnetic radiation in certain characteristic wavelength ranges of the electromagnetic spectrum. Thus, it is possible, for such developing agents, to find at least one wavelength range in which interfering absorption by other constituents of the developing bath is minimal. In this range a spectrophotometric measurement can be made which, after calibration, affords a direct read-off of the concentration of the developing agent that absorbs radiation in that particular range. Depending on the concentration to be measured, and the presence of substances liable to hinder measurement, cells are used that optimize the optical path length of the light absorbed. The power of the radiation source, and the sensitivity of the detector, can also be adjusted.

Figure 1:
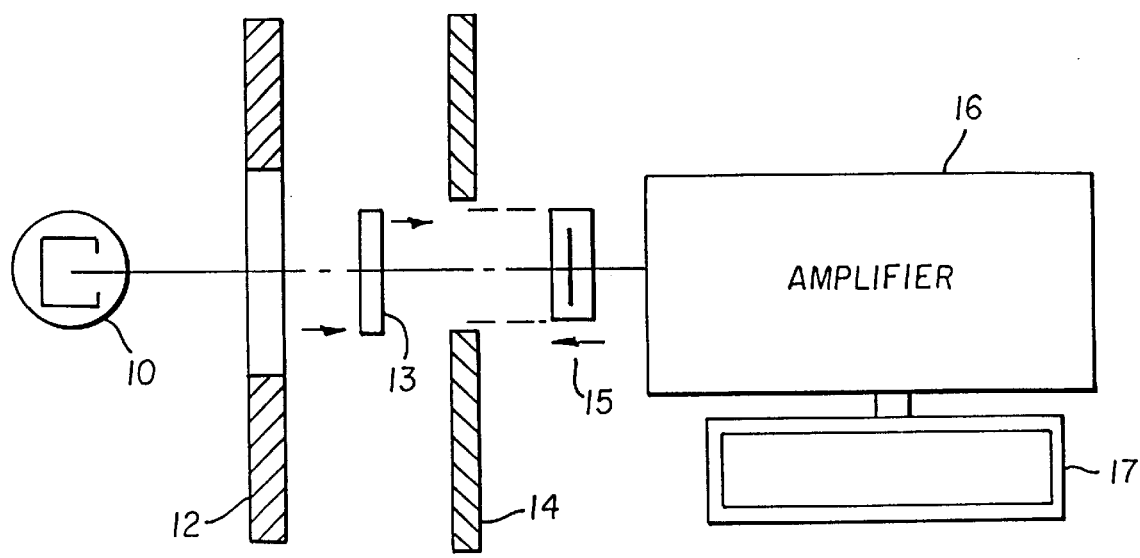
FIG. 1 is a diagram showing an example of a set-up for the implementation of the method according to the invention. This set-up comprises a UV lamp 10, a filter 12, a cell 13 with a sample vessel, a collimator 14, a UV radiation detector 15, an amplifier 16 and a read-out display 17.
Figure 2:
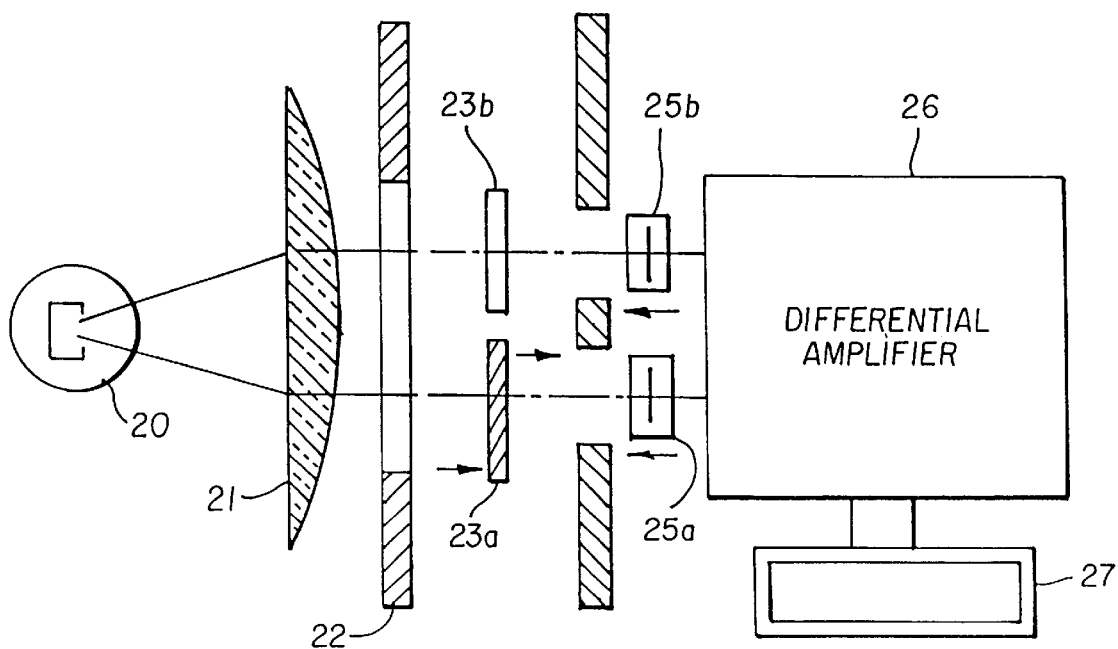
FIG. 2 is a diagram showing another example of a set-up comprising a UV lamp 20, a quartz lens 21, an interferential filter 22, a cell 23a with a vessel containing the developing solution to be tested, a control cell 23b, UV radiation detectors 25a and 25, a differential amplifier 26, and a read-out display 27.
Figure 3:
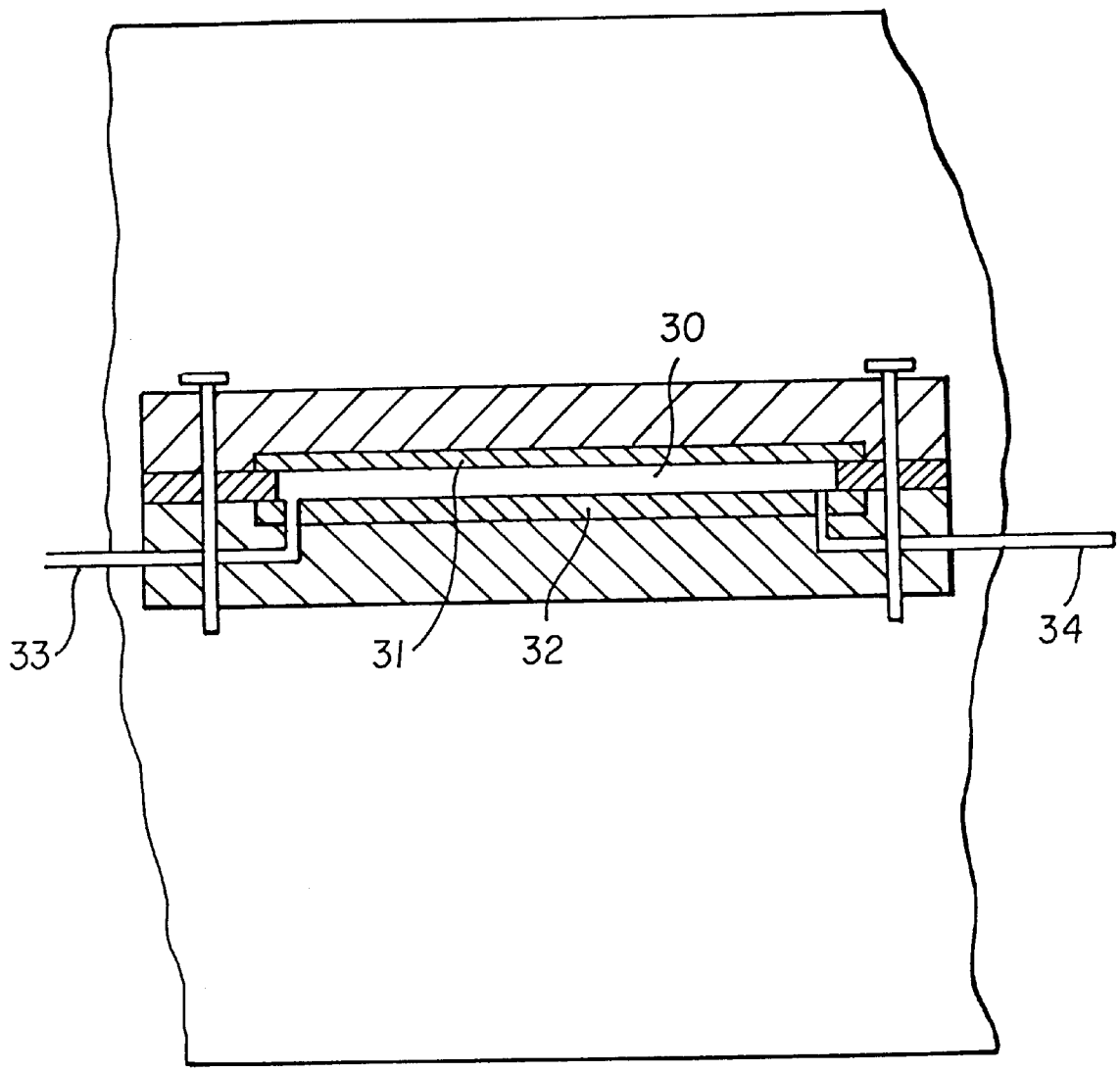
FIG. 3 is a diagram showing a cell such as cell 13 in FIG. 1. This cell comprises a vessel 30 delimited by two quartz plates 31 and 32. The thickness of the vessel and thereby the optical path length of the radiation, can be adjusted. The ducts 33 and 34 allow the developing solution to be fed into the vessel in-process from the photographic processing machine.

Set-ups such as those depicted in FIGS. 1–3 afford in-process measurements, without prior dilution of the developing solution if the thickness of the cell vessel is chosen appropriately.

DETAILED DESCRIPTION OF THE INVENTION

Any suitable spectrophotometric UV source can be used that delivers UV radiation in the range in which the absorption of the substance to be assayed is maximum and specific. For developing agents of the ascorbic acid type, at a wavelength range from 250 nm to 280 nm, and preferably from 260 nm to 270 nm, a specific linear optical density response can be obtained over a useful concentration range of the developing agent in the developing bath.

Developing agents of the ascorbic acid type include ascorbic acid or sterioisomers and diastereoisomers of ascorbic acid, and their sugar-type derivatives or reductone-type derivatives, their salts and mixtures thereof Such developers are well-known in the art as indicated by a number of references, such as Knapp U.S. Pat. No. 5,098,819; Roussilhe U.S. Pat. No. 5,869,223; Newman et al. U.S. Pat. No. 3,942,985, James et al. U.S. Pat. No. 2,688,549, all of which patents are incorporated by reference in their entirety. Such developing agents, for example, indirectly but are not limited to D-isoascorbic acid, D-erythro-acorbic acid, L-ascorbic acid, isoascorbic acid, sorboascorbic acid, d-galactoascorbic acid, etc., and salts of such acids, e.g. sodium or potassium ascorbate, or erythorbate.

In general, the implementation of the method of the invention comprises a method for sampling the developing solution in the developing tank and bringing the sample, for example with a pump, to the measurement cell of the spectrometer. This assembly (sampling, ducting, measurement) can be integrated in an automated developer replenishing device. All that is necessary is that at predetermined values of the spectrophotometric measurements a signal is generated that actuates a replenishing or replacement solution feed system, or which warns the photographic processing maintenance personnel to replenish the developing solution. The method of the invention can also allow continuous monitoring of the concentration of the developing agent, and so of the developing bath activity, or monitoring of the deviation of that concentration from a preset value.

EXAMPLE 1

A sample of developing solution was taken with the following composition:

Ascorbic acid: quantity as given in Table I.

| | |
|---|---|
| Dimezone S (HMMP)[1] | 2.5 g/l |
| Benzotriazole | 0.2 g/l |
| KBr | 4.0 g/l |
| $K_2SO_3$ | 50.0 g/l |
| $K_2CO_3$ | 100.0 g/l |
| NaDTPA[2] 40% solution | 4.3 g/l |
| pH = 10.2 | |

[1]4-hydroxymethyl-4-methyl-1-phenyl-3-pyrazolidone
[2]diethylenetriaminopentaacetic acid sodium salt A sample of this developing solution (see Table I) was diluted in 100 ml of a buffer solution containing 1% sodium sulfite (pH 6.86). This sample of diluted developing solution was placed in the cell vessel of a spectrophotometer (optical path length 2 mm). The measurements of optical density at 264 nm against ascorbic acid concentration are given in Table I below.

TABLE 1

| Developing solution sample ml | Concentration of ascorbic acid g/l | Optical density |
|---|---|---|
| 0.5 | 0.160 | 2.32 |
| 0.4 | 0.128 | 1.91 |
| 0.3 | 0.096 | 1.41 |
| 0.2 | 0.064 | 0.92 |

Figure 4:
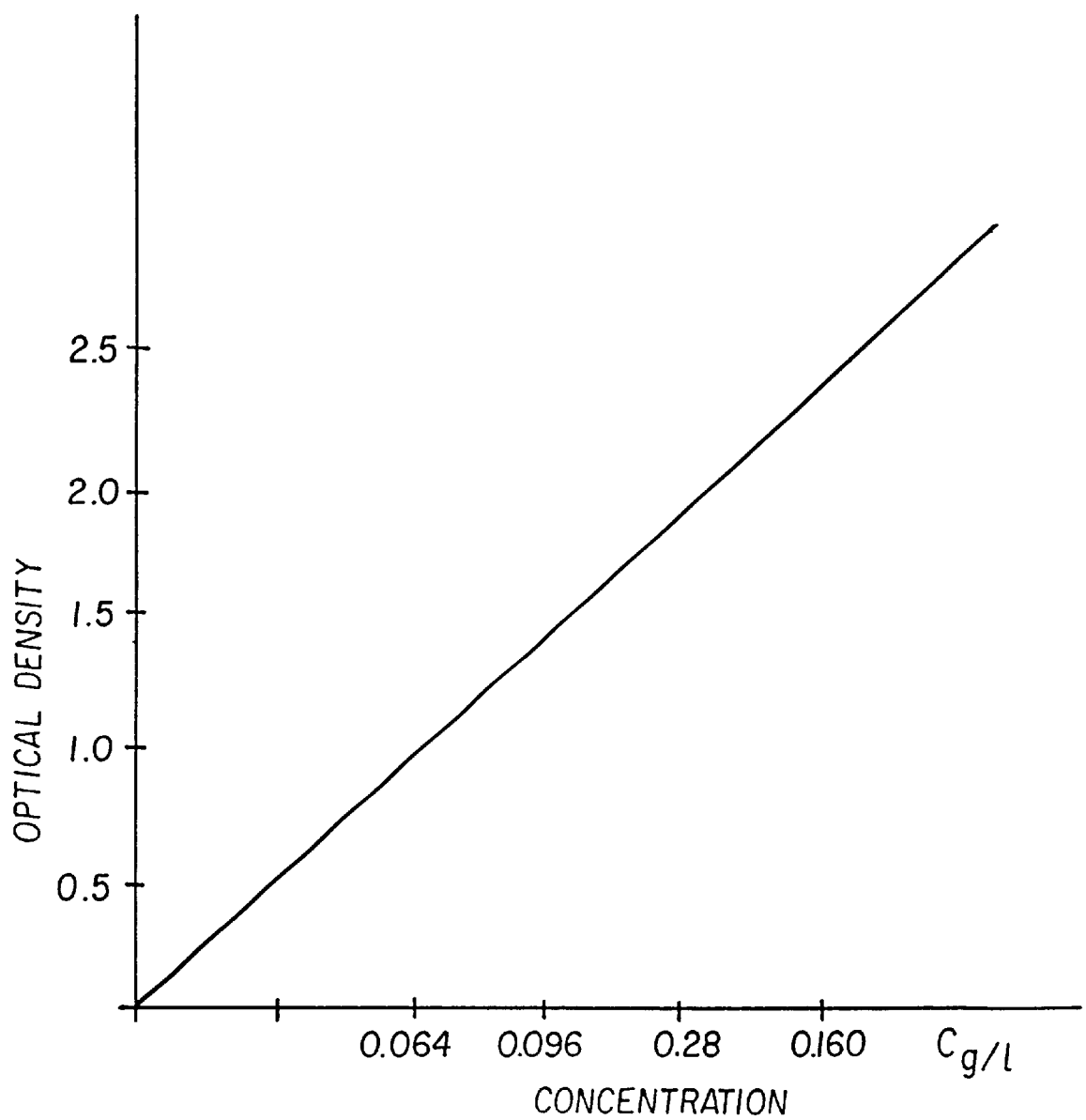
FIG. 4 shows these same results in graph form giving the variation of the optical density D versus the concentration C of ascorbic acid.

These results show that even in the presence of the other constituents of the seasoned developing solution, the spectrophotometric measurement gives a linear response to the ascorbic acid concentration. FIG. 4 shows these same results in graph form giving the variation of the optical density D versus the concentration C of ascorbic acid.

EXAMPLE 2

The operating procedure of Example 1 was used, except that the developing solution contained 7.2 g/l of ascorbic acid, and in place of HMMP, 0.625 g/l of Elon (p-methylaminophenol sulfate). 0.5, 0.4, and 0.3 ml (see Table II below) of this developing solution was diluted in 50 ml of a buffer solution of 0.05 M sodium phosphate containing 1% sodium sulfite (pH 6.86). The spectrophotometric measurements at 264 nm still gave a linear response to the concentration of ascorbic acid, despite the changed chemical environment.

TABLE II

| Developing solution sample ml | Concentration of ascorbic acid g/l | Optical density |
|---|---|---|
| 0.5 | 7.12 | 1.20 |
| 0.4 | 6.0 | 0.97 |
| 0.3 | 4.7 | 0.76 |

EXAMPLE 3

The operating procedure of Example 2 was used, except that the Elon concentration was varied. The spectrophotometry results are given in Table III below:

TABLE III

| Concentration of ascorbic acid g/l | Concentration of Elon g/l | Optical density |
| --- | --- | --- |
| 7.2 | 0.625 | 1.17 |
| 7.2 | 0.520 | 1.15 |
| 7.2 | 0.420 | 1.12 |

Varying the concentration of Elon had practically no impact on the spectrophotometric response.

The invention has been described in detail with particular reference to certain preferred embodiments thereof, but it will be understood that variations and modifications can be effected within the spirit and scope of the invention.

We claim:

1. A method for processing an exposed silver halide photographic material comprising the steps of:

(a) developing of said photographic material in a developing solution containing a silver halide developing agent of the ascorbic acid type;

(b) continuously measuring the concentration of said developing agent of the ascorbic type by ultraviolet spectrophotometry at a wavelength preselected depending on the particular developing agent of the ascorbic type in the range of from 200 to 400 nm; and (c) at a predetermined value of the spectrophotometry measurement, generating a signal that actuates the replenishing of said developing solution.

2. The method of claim 1, wherein the spectrophotometry measurement monitors the deviation of the concentration of the developing agent of the ascorbic acid type from a preset value.

3. The method of claim 1 wherein said developing solution contains a second developing agent that does not interfere with the spectrophotometry measurement of said first developing agent of the ascorbic acid type.

* * * * *